(12) United States Patent
Sakano et al.

(10) Patent No.: US 10,993,648 B2
(45) Date of Patent: May 4, 2021

(54) DRIVING APTITUDE TEST DEVICE AND DRIVING APTITUDE DETERMINATION SYSTEM

(71) Applicant: ALLM INC., Tokyo (JP)

(72) Inventors: Teppei Sakano, Tokyo (JP); Tadashi Masuoka, Kanagawa (JP)

(73) Assignee: ALLM INC., Tokyo (JP)

( * ) Notice: Subject to any disclaimer, the term of this patent is extended or adjusted under 35 U.S.C. 154(b) by 0 days.

(21) Appl. No.: 16/966,108

(22) PCT Filed: Jan. 11, 2019

(86) PCT No.: PCT/JP2019/000651
§ 371 (c)(1),
(2) Date: Jul. 30, 2020

(87) PCT Pub. No.: WO2019/150916
PCT Pub. Date: Aug. 8, 2019

(65) Prior Publication Data
US 2021/0068738 A1 Mar. 11, 2021

(30) Foreign Application Priority Data
Feb. 2, 2018 (JP) .............................. JP2018-016993

(51) Int. Cl.
*G08B 23/00* (2006.01)
*A61B 5/18* (2006.01)
(Continued)

(52) U.S. Cl.
CPC .............. *A61B 5/18* (2013.01); *A61B 5/0042* (2013.01); *A61B 5/055* (2013.01); *G06T 7/0014* (2013.01);
(Continued)

(58) Field of Classification Search
CPC ......... G06T 7/11; G06T 7/174; G06T 7/0014; G06T 7/62; G06T 2207/10081;
(Continued)

(56) References Cited

FOREIGN PATENT DOCUMENTS

| JP | 2005-228003 A | 8/2005 |
|---|---|---|
| JP | 2009-297501 A | 12/2009 |

(Continued)

OTHER PUBLICATIONS

International Search Report (ISR) dated Apr. 9, 2019 filed in PCT/JP2019/000651.
(Continued)

*Primary Examiner* — Dhaval V Patel
(74) *Attorney, Agent, or Firm* — Rankin, Hill & Clark LLP (57) ABSTRACT

The object of the present invention is to assess the driving aptitude of a target person. Provided is a driving aptitude assessment apparatus 200 including: functional impairment degree assessment means configured to assess the degree of functional impairment of a brain of a target person on the basis of test result information indicating a result of a neuropsychological test administered to the target person and head image data obtained by tomography of a head of the target person; and driving aptitude assessment means configured to assess the driving aptitude of the target person on the basis of an assessment result by the functional impairment degree assessment means.

10 Claims, 5 Drawing Sheets

(51) Int. Cl.
    *A61B 5/055*     (2006.01)
    *A61B 5/00*     (2006.01)
    *G06T 7/00*     (2017.01)
    *G16H 50/30*     (2018.01)
    *G06T 7/62*     (2017.01)
    *G06T 7/174*     (2017.01)
    *G06T 7/11*     (2017.01)
    *B60W 40/08*     (2012.01)

(52) U.S. Cl.
    CPC ................ *G06T 7/11* (2017.01); *G06T 7/174* (2017.01); *G06T 7/62* (2017.01); *G16H 50/30* (2018.01); *A61B 2503/08* (2013.01); *B60W 2040/0818* (2013.01); *G06T 2207/10081* (2013.01); *G06T 2207/10088* (2013.01)

(58) Field of Classification Search
    CPC ......... G06T 2207/10088; G16H 50/30; B60W 2040/0818; A61B 5/18; A61B 5/055; A61B 5/0042; A61B 2503/08
    See application file for complete search history.

(56) References Cited

FOREIGN PATENT DOCUMENTS

| | | |
|---|---|---|
| JP | 2011-206452 A | 10/2011 |
| JP | 2012-120823 A | 6/2012 |
| JP | 2015-213539 A | 12/2015 |

OTHER PUBLICATIONS

1st Japanese Office Action (JPOA) dated Jun. 5, 2019 issued in the corresponding Japanese Patent Application No. 2018-016993.
2nd Japanese Office Action dated Sep. 3, 2019 issued in the corresponding Japanese Patent Application No. 2018-016993.
Japanese Decision to Grant dated Nov. 26, 2019 issued in the corresponding Japanese Patent Application No. 2018-016993.

DRIVING APTITUDE TEST DEVICE AND DRIVING APTITUDE DETERMINATION SYSTEM

TECHNICAL FIELD

The present invention relates to a driving aptitude assessment apparatus and a driving aptitude assessment system.

BACKGROUND ART

The following driving aptitude diagnosis apparatus is known: in this driving aptitude diagnosis apparatus, a test subject's reaction to a moving object is measured to diagnose the driving aptitude of the test subject (refer to PATENT LITERATURE 1).

CITATION LIST

Patent Literature

PATENT LIGATURE 1: JP-A-2012-120823

SUMMARY OF INVENTION

Problems to be Solved by Invention

Vehicles are important transportation in our life. However, cognitive functions and physical functions decline with age. Accordingly, in recent years, the number of traffic accidents caused by elderly drivers is on the rise. In order to handle such a problem in Japan, the government imposes a cognitive function test called a screening test prior to a driving lesson for elderly drivers on drivers who are aged 75 years and over at the time of the expiration of the license renewal period. The screening test is conducted by filling in a test form regarding predetermined test items. However, the screening test does not always assess the degree of functional impairment of the brain of a driver with high accuracy. Hence, a technology for assessing a driving aptitude with high accuracy, considering the degree of functional impairment of the brain of a driver, is needed. However, such a method has not at all been studied before.

Solutions to Problems

A driving aptitude assessment apparatus according to a first aspect of the present invention includes: functional impairment degree assessment means configured to assess the degree of functional impairment of a brain of a target person on the basis of test result information indicating a result of a neuropsychological test administered to the target person and head image data obtained by tomography of a head of the target person; and driving aptitude assessment means configured to assess the driving aptitude of the target person on the basis of an assessment result by the functional impairment degree assessment means.

According to a second aspect of the present invention, in the driving aptitude assessment apparatus according to the first aspect, upon an assessment result based on the test result information and an assessment result based on the head image data being different, the functional impairment degree assessment means assesses the assessment result of which degree of functional impairment is severer to be the degree of functional impairment of the brain of the target person.

According to a third aspect of the present invention, in the driving aptitude assessment apparatus according to the first or the second aspect, the functional impairment degree assessment means assesses the degree of functional impairment of the brain of the target person for each cognitive function of the brain, on the basis of the test result information and the head image data.

According to a fourth aspect of the present invention, in the driving aptitude assessment apparatus according to the third aspect, the cognitive functions of the brain include a memory and spatial learning function, a memory storage and retrieval function, a memory and sensory perception function, an executive function, and an information processing function.

According to a fifth aspect of the present invention, in the driving aptitude assessment apparatus according to the third or fourth aspect, the driving aptitude assessment means converts the degree of functional impairment into a numerical form for each cognitive function of the brain of the target person, compares a total value thereof with a preset threshold, and assesses the driving aptitude of the target person.

According to a sixth aspect of the present invention, in the driving aptitude assessment apparatus according to the fifth aspect, the driving aptitude assessment means substitutes a numerical value associated with the degree of functional impairment for the degree, for each cognitive function of the brain of the target person, multiplies the substituted numerical value by a weight value assigned to each cognitive function of the brain, and converts the degree of functional impairment into a numerical form for each cognitive function of the brain of the target person.

According to a seventh aspect of the present invention, a driving aptitude assessment system includes: functional impairment degree assessment means configured to assess the degree of functional impairment of a brain of a target person on the basis of test result information indicating a result of a neuropsychological test administered to the target person and head image data obtained by tomography of a head of the target person; and driving aptitude assessment means configured to assess the driving aptitude of the target person on the basis of an assessment result by the functional impairment degree assessment means.

According to an eighth aspect of the present invention, in the driving aptitude assessment system according to the seventh aspect, upon an assessment result based on the test result information and an assessment result based on the head image data being different, the functional impairment degree assessment means assesses the assessment result of which degree of functional impairment is severer to be the degree of functional impairment of the brain of the target person.

According to a ninth aspect of the present invention, in the driving aptitude assessment system according to the seventh or eighth aspect, the functional impairment degree assessment means assesses the degree of functional impairment of the brain of the target person for each cognitive function of the brain, on the basis of the test result information and the head image data.

According to a tenth aspect of the present invention, in the driving aptitude assessment system according to the ninth aspect, the cognitive functions of the brain include a memory and spatial learning function, a memory storage and retrieval function, a memory and sensory perception function, an executive function, and an information processing function.

According to an eleventh aspect of the present invention, in the driving aptitude assessment system according to the ninth or tenth aspect, the driving aptitude assessment means converts the degree of functional impairment into a numerical form for each cognitive function of the brain of the target person, compares a total value thereof with a preset threshold, and assesses the driving aptitude of the target person.

According to a twelfth aspect of the present invention, in the driving aptitude assessment system according to the eleventh aspect, the driving aptitude assessment means substitutes a numerical value associated with the degree of functional impairment for the degree, for each cognitive function of the brain of the target person, multiplies the substituted numerical value by a weight value assigned to each cognitive function of the brain, and converts the degree of functional impairment into a numerical form for each cognitive function of the brain of the target person.

Effects of Invention

According to the present invention, it is configured in such a manner that the degree of functional impairment of the brain of a target person is assessed on the basis of a result of a neuropsychological test of the target person and head image data obtained by tomography of the head of the target person to assess the driving aptitude of the target person; accordingly, the driving aptitude of the target person can be assessed with high accuracy.

DESCRIPTION OF EMBODIMENTS

Figure 1:
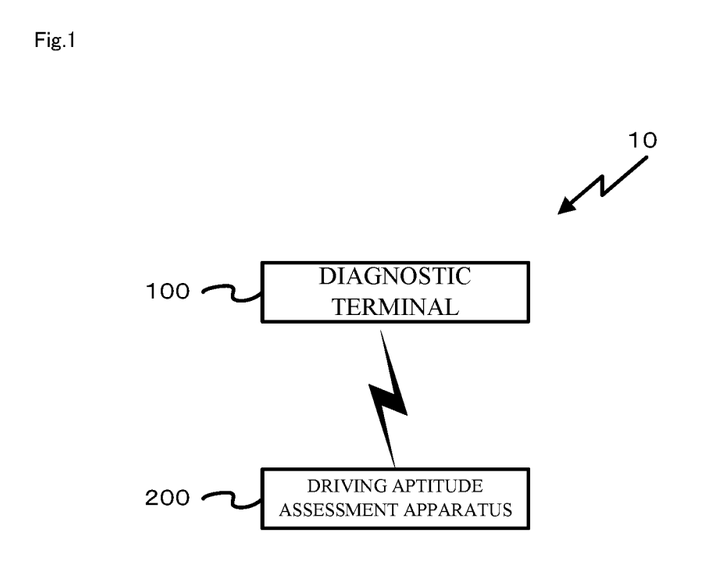
FIG. 1 is a block diagram illustrating the configuration of one embodiment of a driving aptitude assessment system 10.

FIG. 1 is a block diagram illustrating the configuration of one embodiment of a driving aptitude assessment system 10 in the embodiment. In the driving aptitude assessment system 10, a diagnostic terminal 100 that is operated by a diagnoser who diagnoses the driving aptitude of a target person, and a driving aptitude assessment apparatus 200 that receives data from the diagnostic terminal 100 and executes a process for assessing the driving aptitude of the target person are connected via a communications line.

In the embodiment, for example, an elderly person who may have a doubt or problem in driving aptitude is assumed to be a target person. Moreover, the diagnostic terminal 100 is, for example, installed in a hospital to be operated by a doctor who diagnoses senile dementia of an elderly person, or installed in, for example, an institution that needs to grasp the driving aptitude of an elderly person.

Figure 2:
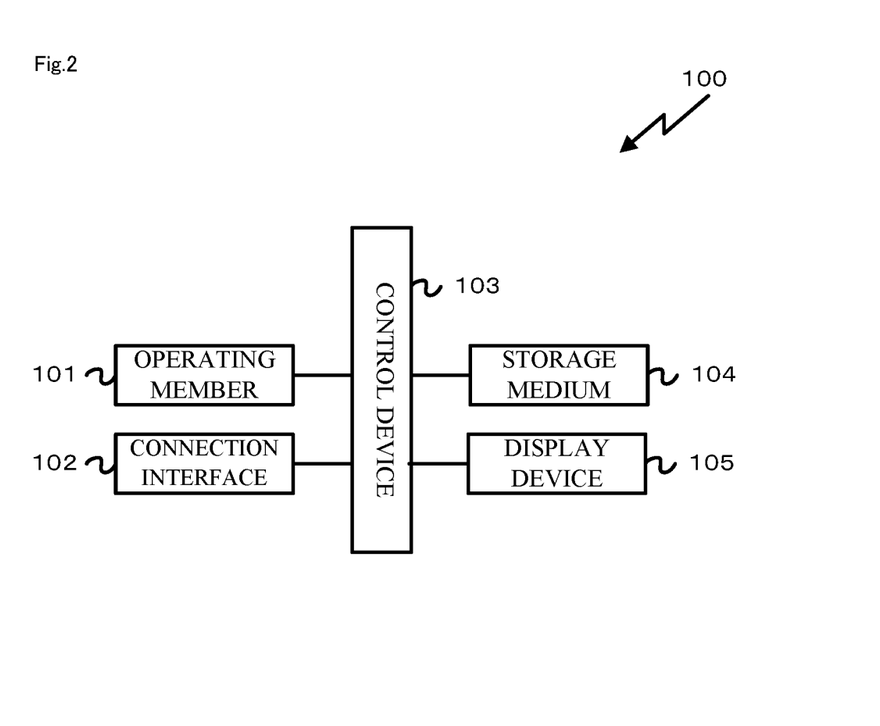
FIG. 2 is a block diagram illustrating the configuration of one embodiment of a diagnostic terminal 100.

For example, a smartphone, a mobile phone, a tablet terminal, or a personal computer is used as the diagnostic terminal 100. FIG. 2 is a block diagram illustrating the configuration of one embodiment in a case of using a personal computer as the diagnostic terminal 100 in the embodiment.

The diagnostic terminal 100 includes an operating member 101, a connection interface 102, a control device 103, a storage medium 104, and a display device 105.

The operating member 101 includes various devices that are operated by an operator of the diagnostic terminal 100, for example, a keyboard and a mouse.

The connection interface 102 is an interface for connecting the diagnostic terminal 100 to external apparatuses such as other apparatuses and terminals. The connection interface 102 includes, for example, an interface for connecting to communications lines such as a LAN and the Internet. The diagnostic terminal 100 communicates with the driving aptitude assessment apparatus 200 via the connection interface 102.

The control device 103 includes a CPU, memory, and other peripheral circuits, and controls the entire diagnostic terminal 100. The memory configuring the control device 103 is volatile memory such as SDRAM. The memory is used as work memory for developing a program when the CPU executes the program, and buffer memory for temporarily recording data. For example, data that has been read in via the connection interface 102 is temporarily recorded in the buffer memory.

The storage medium 104 is a storage medium for recording, for example, various kinds of data stored in the diagnostic terminal 100, and data of a program to be executed by the control device 103. For example, an HDD (Hard Disk Drive) or SSD (Solid State Drive) is used as the storage medium 104. The data of the program recorded in the storage medium 104 is provided, recorded in a recording medium such as a CD-ROM or DVD-ROM, or via a network. The data of the program acquired by an operator is installed onto the storage medium 104, which enables the control device 103 to execute the program.

The display device 105 is, for example, a liquid crystal monitor, and displays various kinds of display data that are outputted from the control device 103.

Figure 3:
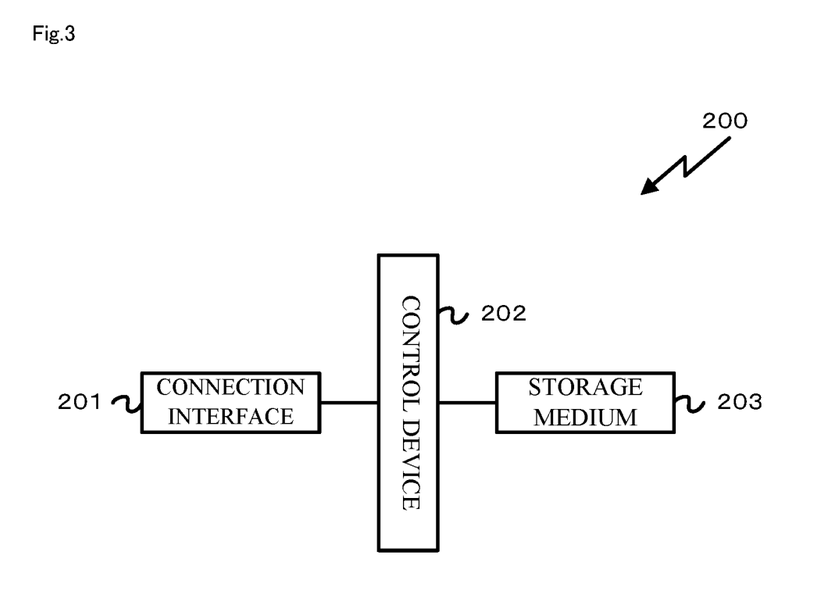
FIG. 3 is a block diagram illustrating the configuration of one embodiment of a driving aptitude assessment apparatus 200.

The driving aptitude assessment apparatus 200 is an apparatus connected to the Internet. For example, a personal computer or server is used as the driving aptitude assessment apparatus 200. FIG. 3 is a block diagram illustrating the configuration of one embodiment in a case of using a server apparatus as the driving aptitude assessment apparatus 200 in the embodiment. The driving aptitude assessment apparatus 200 includes a connection interface 201, a control device 202, and a storage medium 203.

The connection interface 201 is an interface for connecting the driving aptitude assessment apparatus 200 to a communications line such as the Internet. For example, a wired LAN module for connecting by wire to the Internet, or a wireless LAN module for connecting wirelessly to the Internet, is used as the connection interface 201. In the embodiment, the driving aptitude assessment apparatus 200 communicates with the diagnostic terminal 100 via the connection interface 201.

The control device 202 includes a CPU, memory, and other peripheral circuits, and controls the entire driving aptitude assessment apparatus 200. The memory configuring the control device 202 is volatile memory such as SDRAM. The memory is used as work memory for developing a program when the CPU executes the program, and buffer memory for temporarily recording data. For example, data that has been read in via the connection interface 201 is temporarily recorded in the buffer memory.

The storage medium 203 is a storage medium for recording, for example, various kinds of data stored in the driving aptitude assessment apparatus 200, and data of a program to be executed by the control device 202. For example, an HDD (Hard Disk Drive) or SSD (Solid State Drive) is used as the storage medium 203. The data of the program recorded in the storage medium 203 is provided, recorded in a recording medium such as a CD-ROM or DVD-ROM, or via a network. The data of the program acquired by an operator is installed onto the storage medium 203, which enables the control device 202 to execute the program.

The driving aptitude assessment system 10 in the embodiment provides a mechanism for assessing the degree of functional impairment of the brain of a target person, and assessing the driving aptitude of the target person on the basis of the assessment result.

In the embodiment, a neuropsychological test is administered in advance to a target person to be a target for assessing an aptitude for driving, and then test result information indicating a result of the neuropsychological test is recorded in the storage medium 203 of the driving aptitude assessment apparatus 200. Moreover, head image data obtained by tomography of the head of the target person is acquired and recorded in advance in the storage medium 203 of the driving aptitude assessment apparatus 200.

The control device 202 executes a process described below to assess the degree of functional impairment of the brain of the target person on the basis of the neuropsychological test result and head image data of the target person and then assess the driving aptitude of the target person on the basis of the assessment result.

It may be configured in such a manner that test result information indicating the neuropsychological test result and the head image data obtained by tomography of the head of the target person are inputted on the diagnostic terminal 100, and transmitted to the driving aptitude assessment apparatus 200 to be recorded in the storage medium 203. Alternatively, it may be configured in such a manner that the test result information and the head image data are inputted on a terminal different from the diagnostic terminal 100, and transmitted to the driving aptitude assessment apparatus 200 to be recorded in the storage medium 203. Alternatively, they may be inputted directly on the driving aptitude assessment apparatus 200.

In the embodiment, the operator of the diagnostic terminal 100 can provide an instruction to assess the driving aptitude of the target person on the basis of the test result information indicating the neuropsychological test result and the head image data obtained by tomography of the head of the target person, by operating the operating member 101. The control device 103 instructs the driving aptitude assessment apparatus 200 to start assessing the driving aptitude of the target person when instructed to assess the driving aptitude of the target person. When the driving aptitude assessment apparatus 200 is instructed by the diagnostic terminal 100 to start assessing the driving aptitude of the target person, the control device 202 executes the process described below and assesses the driving aptitude of the target person. The process for assessing the driving aptitude of the target person, which is executed by the control device 202, is described below.

The test result information of the neuropsychological test is information indicating the result of the neuropsychological test administered to the target person by a healthcare worker such as a doctor or nurse. In the embodiment, the control device 202 assesses the degree of functional impairment of the brain of the target person for each cognitive function of the brain, on the basis of the test result information of the neuropsychological test. The cognitive functions of the brain include a memory and spatial learning function, a memory storage and retrieval function, a memory and sensory perception function, an executive function, and an information processing function. A specific example of the contents of the neuropsychological test and a process for assessing the degree of functional impairment of the brain of the target person for each cognitive function of the brain on the basis of the test result information in the embodiment are described below.

In the embodiment, information indicating a correct or wrong answer to each of test items 1 to 14 presented below is recorded in the storage medium 203 as the test result information of the neuropsychological test of the target person:

Test Item 1: It should be scored as correct if a circle representing a clock is drawn for a test item that asks the target person to "draw a clock."

Test Item 2: It should be scored as correct if the numbers are drawn on the clock for the test item that asks him/her to "draw a clock."

Test Item 3: It should be scored as correct if the hands are drawn on the clock for the test item that asks him/her to "draw a clock."

Test Item 4: Show a picture of a trumpet. It should be scored as correct if he/she remembers the picture and recognizes it as a musical instrument.

Test Item 5: Show a picture of a beetle. It should be scored as correct if he/she remembers the picture and recognizes it as an insect.

Test Item 6: Show a picture of a pineapple. It should be scored as correct if he/she remembers the picture and recognizes it as a fruit.

Test Item 7: Show a picture of a horse. It should be scored as correct if he/she remembers the picture and recognizes it as an animal.

Test Item 8: Ask the present year. It is scored as correct when the year is answered correctly.

Test Item 9: Ask the present month. It is scored as correct when the month is answered correctly.

Test Item 10: Ask the present date. It is scored as correct when the date is answered correctly.

Test Item 11: Ask the current time. It is scored as correct when the time is answered correctly.

Test Item 12: Ask the present day of the week. It is scored as correct when the day of the week is answered correctly.

Test Item 13: Tell the target person a specific number. It should be scored as correct if he/she can find the number quickly from a list of numbers.

Test Item 14: Instruct him/her to perform a specific action, for example, raising his/her hand or reading a sentence. It should be scored as correct if he/she can act as instructed.

The control device 202 assesses the degree of impairment of the memory and spatial learning function among the cognitive functions of the brain of the target person, on the basis of test results of test items 1 to 3. For example, if the percentage of correct answers to test items 1 to 3 is less than 30%, the degree of impairment of the memory and spatial learning function of the target person is assessed to be severe. If the percentage of correct answers to test items 1 to 3 is equal to or greater than 30% and less than 50%, the degree of impairment of the memory and spatial learning function of the target person is assessed to be moderate. If the percentage of correct answers to test items 1 to 3 is equal to or greater than 50% and less than 80%, the degree of impairment of the memory and spatial learning function of the target person is assessed to be mild. If the percentage of correct answers to test items 1 to 3 is equal to or greater than 80%, the memory and spatial learning function of the target person is assessed to be intact.

The control device 202 assesses the degree of impairment of the memory storage and retrieval function among the cognitive functions of the brain of the target person, on the basis of test results of test items 4 to 7. For example, if the percentage of correct answers to test items 4 to 7 is less than 40%, the degree of impairment of the memory storage and retrieval function of the target person is assessed to be severe. If the percentage of correct answers to test items 4 to 7 is equal to or greater than 40% and less than 60%, the degree of impairment of the memory storage and retrieval function of the target person is assessed to be moderate. If the percentage of correct answers to test items 4 to 7 is equal to or greater than 60% and less than 80%, the degree of impairment of the memory storage and retrieval function of the target person is assessed to be mild. If the percentage of correct answers to test items 4 to 7 is equal to or greater than 80%, the memory storage and retrieval function of the target person is assessed to be intact.

The control device 202 assesses the degree of impairment of the memory and sensory perception function among the cognitive functions of the brain of the target person, on the basis of test results of test items 1 to 7. For example, if the percentage of correct answers to test items 1 to 7 is less than 30%, the degree of impairment of the memory and sensory perception function of the target person is assessed to be severe. If the percentage of correct answers to test items 1 to 7 is equal to or greater than 30% and less than 50%, the degree of impairment of the memory and sensory perception function of the target person is assessed to be moderate. If the percentage of correct answers to test items 1 to 7 is equal to or greater than 50% and less than 80%, the degree of impairment of the memory and sensory perception function of the target person is assessed to be mild. If the percentage of correct answers to test items 1 to 7 is equal to or greater than 80%, the memory and sensory perception function of the target person is assessed to be intact.

The control device 202 assesses the degree of impairment of the executive function among the cognitive functions of the brain of the target person, on the basis of test results of test items 13 and 14. For example, if the percentage of correct answers to test items 13 and 14 is less than 40%, the degree of impairment of the executive function of the target person is assessed to be severe. If the percentage of correct answers to test items 13 and 14 is equal to or greater than 40% and less than 60%, the degree of impairment of the memory executive function of the target person is assessed to be moderate. If the percentage of correct answers to test items 13 and 14 is equal to or greater than 60% and less than 80%, the degree of impairment of the executive function of the target person is assessed to be mild. If the percentage of correct answers to test items 13 and 14 is equal to or greater than 80%, the executive function of the target person is assessed to be intact.

The control device 202 assesses the degree of impairment of the information processing function among the cognitive functions of the brain of the target person, on the basis of test results of test items 8 to 13. For example, if the percentage of correct answers to test items 8 to 13 is less than 40%, the degree of impairment of the information processing function of the target person is assessed to be severe. If the percentage of correct answers to test items 8 to 13 is equal to or greater than 40% and less than 60%, the degree of impairment of the information processing function of the target person is assessed to be moderate. If the percentage of correct answers to test items 8 to 13 is equal to or greater than 60% and less than 80%, the degree of impairment of the information processing function of the target person is assessed to be mild. If the percentage of correct answers to test items 8 to 13 is equal to or greater than 80%, the information processing function of the target person is assessed to be intact.

The above-mentioned test contents and assessment method are examples. The contents of the neuropsychological test are not limited to the above test contents as long as the contents can be used to assess the driving aptitude of the target person. Moreover, the thresholds for the percentage of correct answers used to assess the degree of functional impairment of each cognitive function of the brain of the target person to be severe, moderate, or mild are assumed to be set and recorded in advance in the storage medium 203. Moreover, the thresholds may be fixed values, or be freely changeable. Moreover, the above thresholds are merely examples, and are not limited to the above values.

The head image data obtained by tomography of the head of the target person is assumed to be, for example, a CT image or MRI image of the head of the target person. In the embodiment, a CT image or MRI image including a plurality of cross-sectional images obtained by imaging cross sectional slices of the head of the target person with a predetermined slice thickness is acquired and recorded in advance in the storage medium 203. The number of cross-sectional images configuring the head image data of the target person depends on the number of slices imaged upon imaging. The number of slices imaged changes depending on the performance and settings of an imaging machine.

The process for assessing the degree of functional impairment of the brain of the target person for each cognitive function of the brain on the basis of the head image data of the target person in the embodiment is described below.

The control device 202 analyzes the head image data of the target person and determines the size of each region of the brain of the target person. In the embodiment, the size is determined for each of regions of the hippocampus governing the memory and spatial learning function among the cognitive functions of the brain, the frontal association area governing the executive function among the cognitive functions of the brain, the temporal association area governing the memory and sensory perception function among the cognitive functions of the brain, the parahippocampal gyrus governing the memory storage and retrieval function among the cognitive functions of the brain, and the amygdala governing the information processing function among the cognitive functions of the brain. In the embodiment, an example where the sizes of the five regions of the hippocampus, the frontal association area, the temporal association area, the parahippocampal gyms, and the amygdala are determined is described. However, the regions are not limited to the above regions as long as the degree of impairment of the brain cognitive function of the target person can be assessed.

In the embodiment, the regions such as the hippocampus, the frontal association area, the temporal association area, the parahippocampal gyrus, and the amygdala have substantially a fixed shape. Accordingly, matching images mimicking the shapes of these regions are prepared and recorded in advance in the storage medium 203. The control device 202 performs a matching process using the matching images on the head image data of the target person, and extracts areas of the above five regions in the head image data of the target person. The control device 202 then determines the volume of each extracted region, and determines the size of the region. The volume of each region of the head image data of the target person can be calculated by multiplying the area of each region by the slice thickness for each cross-sectional image configuring the head image data of the target person, obtaining the volume per cross-sectional image, and adding up the total volume of the slices, that is, the cross-sectional images configuring the head image data of the target person.

The control device 202 compares the size of each region of the brain of the target person calculated on the basis of the head image data of the target person with a standard size of the region to calculate the degree of atrophy of the region of the brain of the target person. The control device 202 then compares the calculated degree of atrophy with preset thresholds that are used to assess the degree of cognitive function impairment, and assesses the degree of functional impairment of the brain of the target person for each cognitive function of the brain. The standard size of each region and the thresholds used for assessment are recorded in advance in the storage medium 203. A specific assessment method is described below. However, the standard size of each region and the thresholds used for assessment, which are described below, are examples, and the sizes and thresholds are not limited to those described below.

The standard size of the hippocampus region is assumed to be, for example, 40 cc. In this case, the control device 202 assesses the degree of impairment of the memory and spatial learning function of the brain of the target person as follows: If the size of the hippocampus region of the brain of the target person has shrunk by equal to or greater than 15% compared with the standard size, the degree of impairment of the memory and spatial learning function of the brain of the target person is assessed to be severe. If the degree of atrophy in the size of the hippocampus region of the brain of the target person is equal to or greater than 10% and less than 15% compared with the standard size, the degree of impairment of the memory and spatial learning function of the brain of the target person is assessed to be moderate. If degree of atrophy in the size of the hippocampus region of the brain of the target person is equal to or greater than 5% and less than 10% compared with the standard size, the degree of impairment of the memory and spatial learning function of the brain of the target person is assessed to be mild. If the degree of atrophy in the size of the hippocampus region of the brain of the target person is less than 5% compared with the standard size, the memory and spatial learning function of the brain of the target person is assessed to be intact.

The standard size of the frontal association area region is assumed to be, for example, 50 cc. In this case, the control device 202 assesses the degree of impairment of the executive function of the brain of the target person as follows: If the size of the frontal association area region of the brain of the target person has shrunk by equal to or greater than 20% compared with the standard size, the degree of impairment of the executive function of the brain of the target person is assessed to be severe. If the degree of atrophy in the size of the frontal association area region of the brain of the target person is equal to or greater than 15% and less than 20% compared with the standard size, the degree of impairment of the executive function of the brain of the target person is assessed to be moderate. If the degree of atrophy in the size of the frontal association area region of the brain of the target person is equal to or greater than 10% and less than 15% compared with the standard size, the degree of impairment of the executive function of the brain of the target person is assessed to be mild. If the degree of atrophy in the size of the frontal association area region of the brain of the target person is less than 10% compared with the standard size, the executive function of the brain of the target person is assessed to be intact.

The standard size of the temporal association area region is assumed to be, for example, 50 cc. In this case, the control device 202 assesses the degree of impairment of the memory and sensory perception function of the brain of the target person as follows: If the size of the temporal association area region of the brain of the target person has shrunk by equal to or greater than 20% compared with the standard size, the degree of impairment of the memory and sensory perception function of the brain of the target person is assessed to be severe. If the degree of atrophy in the size of the temporal association area region of the brain of the target person is equal to or greater than 15% and less than 20% compared with the standard size, the degree of impairment of the memory and sensory perception function of the brain of the target person is assessed to be moderate. If the degree of atrophy in the size of the temporal association area region of the brain of the target person is equal to or greater than 10% and less than 15% compared with the standard size, the degree of impairment of the memory and sensory perception function of the brain of the target person is assessed to be mild. If the degree of atrophy in the size of the temporal association area region of the brain of the target person is less than 10% compared with the standard size, the memory and sensory perception function of the brain of the target person is assessed to be intact.

The standard size of the parahippocampal gyms region is assumed to be, for example, 100 cc. In this case, the control device 202 assesses the degree of impairment of the memory storage and retrieval function of the brain of the target person as follows: If the size of the parahippocampal gyms region of the brain of the target person has shrunk by equal to or greater than 30% compared with the standard size, the degree of impairment of the memory storage and retrieval function of the brain of the target person is assessed to be severe. If the degree of atrophy in the size of the parahippocampal gyrus region of the brain of the target person is equal to or greater than 20% and less than 30% compared with the standard size, the degree of impairment of the memory storage and retrieval function of the brain of the target person is assessed to be moderate. If the degree of atrophy in the size of the parahippocampal gyrus region of the brain of the target person is equal to or greater than 10% and less than 20% compared with the standard size, the degree of impairment of the memory storage and retrieval function of the brain of the target person is assessed to be mild. If the degree of atrophy in the size of the parahippocampal gyrus region of the brain of the target person is less than 10% compared with the standard size, the memory storage and retrieval function of the brain of the target person is assessed to be intact.

The standard size of the amygdala region is assumed to be, for example, 70 cc. In this case, the control device 202 assesses the degree of impairment of the information processing function of the brain of the target person as follows: If the size of the amygdala region of the brain of the target person has shrunk by equal to or greater than 30% compared with the standard size, the degree of impairment of the information processing function of the brain of the target person is assessed to be severe. If the degree of atrophy in the size of the amygdala region of the brain of the target person is equal to or greater than 20% and less than 30% compared with the standard size, the degree of impairment of the information processing function of the brain of the target person is assessed to be moderate. If the degree of atrophy in the size of the amygdala region of the brain of the target person is equal to or greater than 10% and less than 20% compared with the standard size, the degree of impairment of the information processing function of the brain of the target person is assessed to be mild. If the degree of atrophy in the size of the amygdala region of the brain of the target person is less than 10% compared with the standard size, the information processing function of the brain of the target person is assessed to be intact.

The control device 202 assesses the degree of functional impairment for each cognitive function of the brain of the target person, on the basis of the degree of functional impairment of each cognitive function of the brain based on the test result information of the neuropsychological test of the target person, and the degree of functional impairment of each cognitive function of the brain based on the head image data of the target person. In the embodiment, in terms of each cognitive function of the brain, if the assessment result based on the test result information of the neuropsychological test agrees with the assessment result based on the head image data, the control device 202 employs the assessment result. If the assessment result based on the test result information of the neuropsychological test does not agree with the assessment result based on the head image data, the control device 202 employs the assessment result indicating severer impairment.

For example, it is assumed that the degree of functional impairment of each cognitive function of the brain of a certain target person has been assessed to be mild in the memory and spatial learning function, severe in the memory storage and retrieval function, mild in the memory and sensory perception function, moderate in the executive function, and moderate in the information processing function, on the basis of test result information of a neuropsychological test of the target person. Moreover, it is assumed that the degree of functional impairment of each cognitive function of the brain of the same target person has been assessed to be severe in the memory and spatial learning function, moderate in the memory storage and retrieval function, mild in the memory and sensory perception function, intact in the executive function, and mild in the information processing function, on the basis of head image data of the target person. In this case, the degree of functional impairment of each cognitive function of the brain of the target person is assessed to be severe in the memory and spatial learning function, severe in the memory storage and retrieval function, mild in the memory and sensory perception function, moderate in the executive function, and moderate in the information processing function.

The control device 202 substitutes a numerical value associated with the degree of functional impairment of each cognitive function of the brain of the target person assessed in the above-mentioned process, for the degree. The control device 202 then multiplies the substituted numerical value by a weight value set for each cognitive function to convert the degree of functional impairment into a numerical form for each cognitive function of the brain of the target person. The weight value is preset in accordance with a risk that the degree of cognitive function impairment affects the driving aptitude. The control device 202 then compares a total value of the numerical values determined respectively for the cognitive functions with preset thresholds to assess the driving aptitude of the target person.

In the embodiment, a numerical value is assigned to the degree of functional impairment of each cognitive function, for example, three in a case of severe impairment, two in a case of moderate impairment, one in a case of mild impairment, and zero in a case of intact functioning. Moreover, a weight value of two is set for the memory and spatial learning function, a weight value of three for the memory storage and retrieval function, a weight value of two for the memory and sensory perception function, a weight value of one for the executive function, and a weight value of one for the information processing function. Thresholds are set in such a manner that if the total value is equal to or greater than 20, the target person is assessed to not have an aptitude for driving, if the total value is equal to or greater than 15 and less than 20, the driving aptitude of the target person is assessed to be doubtful, and if the total value is less than 15, the target person is assessed to have no problem in driving aptitude. The numerical values in accordance with the degrees of functional impairment, the weight value for each cognitive function, and the thresholds used to assess the driving aptitude are recorded in advance in the storage medium 203. The above numerical values in accordance with the degrees of functional impairment, weight value for each cognitive function, and thresholds used to assess the driving aptitude are examples. The numerical values in accordance with degrees of functional impairment, the weight value for each cognitive function, and the thresholds used to assess the driving aptitude are not limited to the above examples.

As described above, the control device 202 calculates a total value of the cognitive functions of the brain of the target person from the following equations (1) to (6), for example, if the degree of functional impairment of each cognitive function of the brain of the target person is assessed to be severe in the memory and spatial learning function, severe in the memory storage and retrieval function, mild in the memory and sensory perception function, moderate in the executive function, and moderate in the information processing function. In the following equations (1) to (5), numerical values within parentheses indicate a numerical value and weight value in accordance with the degree of impairment.

$$\text{Memory and spatial learning function} = \text{severe } (3) \times \text{weight value } (2) = 6 \quad (1)$$

$$\text{Memory storage and retrieval function} = \text{severe } (3) \times \text{weight value } (3) = 9 \quad (2)$$

$$\text{Memory and sensory perception function} = \text{mild } (1) \times \text{weight value } (2) = 2 \quad (3)$$

$$\text{Executive function} = \text{moderate } (2) \times \text{weight value } (1) = 2 \quad (4)$$

$$\text{Information processing function} = \text{moderate } (2) \times \text{weight value } (1) = 2 \quad (5)$$

$$\text{Total value of the cognitive functions of the brain of the target person} = 6+9+2+2+2 = 21 \quad (6)$$

The control device 202 compares the calculation result of equation (6) with the thresholds for driving aptitude assessment recorded in the storage medium 203, and assesses the driving aptitude of the target person. According to the calculation result of equation (6), the target person is assessed to not have an aptitude for driving. The control device 202 then transmits the result of assessing the driving aptitude of the target person to the diagnostic terminal 100.

In the diagnostic terminal 100, the control device 103 displays, on the display device 105, the result of assessing the driving aptitude of the target person received from the driving aptitude assessment apparatus 200. Consequently, the operator of the diagnostic terminal 100 can grasp the result of assessing the driving aptitude of the target person.

Moreover, the operator of the diagnostic terminal 100 can offer the target person guidance and treatment based on his/her driving aptitude.

Figure 4:
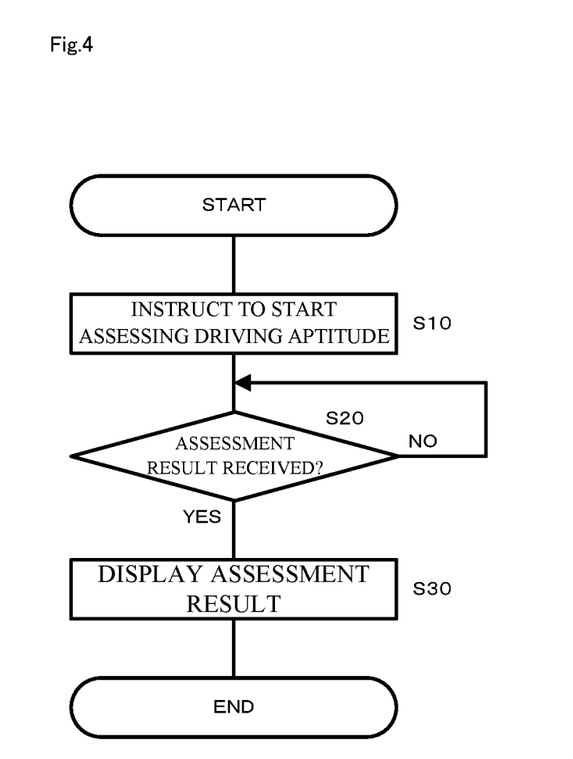
FIG. 4 is a flowchart illustrating the flow of a process that is executed by the diagnostic terminal 100.

FIG. 4 is a flowchart illustrating the flow of a process that is executed by the diagnostic terminal 100 in the embodiment. The process illustrated in FIG. 4 is executed by the control device 103 as a program that starts when the operator provides an instruction to assess the driving aptitude of a target person.

In step S10, the control device 103 instructs the driving aptitude assessment apparatus 200 to start assessing the driving aptitude of the target person, and then proceeds to step S20.

In step S20, the control device 103 judges whether or not to have received a result of assessing the driving aptitude of the target person from the driving aptitude assessment apparatus 200. In a case of an affirmative judgement in step S20, proceed to step S30.

In step S30, the control device 103 displays, on the display device 105, the result of assessing the driving aptitude of the target person received from the driving aptitude assessment apparatus 200, and then ends the process.

Figure 5:
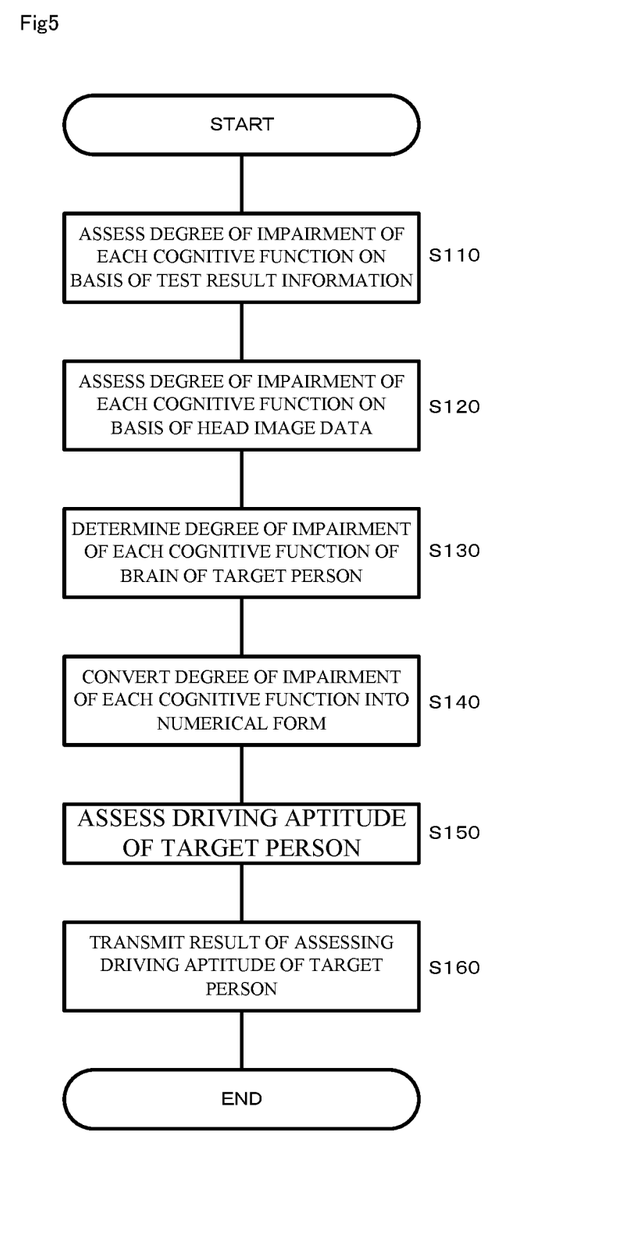
FIG. 5 is a flowchart illustrating the flow of a process that is executed by the driving aptitude assessment apparatus 200.

FIG. 5 is a flowchart illustrating the flow of a process that is executed by the driving aptitude assessment apparatus 200 in the embodiment. The process illustrated in FIG. 5 is executed by the control device 202 as a program that starts when the diagnostic terminal 100 provides an instruction to start assessing the driving aptitude of a target person.

In step S110, as described above, the control device 202 assesses the degree of impairment of each cognitive function of the brain of the target person, on the basis of test result information indicating a result of a neuropsychological test of the target person, and then proceeds to step S120.

In step S120, as described above, the control device 202 assesses the degree of impairment of each cognitive function of the brain of the target person, on the basis of head image data obtained by tomography of the head of the target person, and then proceeds to step S130.

In step S130, as described above, in terms of each cognitive function of the brain, if the assessment result based on the test result information of the neuropsychological test agrees with the assessment result based on the head image data, the control device 202 employs the assessment result. If the assessment result based on the test result information of the neuropsychological test does not agree with the assessment result based on the head image data, the control device 202 employs the assessment result indicating severer impairment. Accordingly, the control device 202 determines the degree of impairment of each cognitive function of the brain of the target person, and then proceeds to step S140.

In step S140, as described above, the control device 202 substitutes a numerical value associated with the degree of functional impairment of each cognitive function of the brain of the target person, for the degree. The control device 202 multiplies the substituted numerical value by the preset weight value to convert the degree of functional impairment into a numerical form for each cognitive function of the brain of the target person, and then proceeds to step S150.

In step S150, the control device 202 compares a total value of the numerical values determined respectively for the cognitive functions with the preset thresholds to assess the driving aptitude of the target person, and then proceeds to step S160.

In step S160, the control device 202 transmits a result of assessing the driving aptitude of the target person to the diagnostic terminal 100, and then ends the process.

According to the above-described embodiment, the following operations and effects can be obtained:

(1) The control device 202 is configured in such a manner as to assess the degree of functional impairment of the brain of a target person on the basis of test result information indicating a result of a neuropsychological test administered to the target person, and head image data obtained by tomography of the head of the target person, and assess the driving aptitude of the target person on the basis of a result of assessing the degree of functional impairment of the brain of the target person. Consequently, it is possible to assess the driving aptitude of the target person with higher accuracy than to assess the driving aptitude of the target person on the basis of one of the result of the neuropsychological test administered to the target person, and the head image data obtained by tomography of the head of the target person.

(2) The control device 202 is configured in such a manner as to, if the assessment result based on the test result information and the assessment result based on the head image data are different, determine the assessment result of which degree of functional impairment is severer as the degree of functional impairment of the brain of the target person. Consequently, even if the assessment result based on the test result information and the assessment result based on the head image data are different, it is possible to assess the driving aptitude of the target person with high accuracy.

(3) The control device 202 is configured in such a manner as to assess the degree of functional impairment of the brain of the target person for each cognitive function of the brain, on the basis of the test result information and the head image data. Consequently, it is possible to assess the degree of functional impairment for each cognitive function of the brain that may affect the driving aptitude.

(4) The control device 202 is configured in such a manner as to convert the degree of functional impairment into a numerical form for each cognitive function of the brain of the target person, compare a total value thereof with preset thresholds, and accordingly assess the driving aptitude of the target person. In this manner, the degree of functional impairment is converted into a numerical form for each cognitive function of the brain of the target person; accordingly, it is possible to assess the driving aptitude of the target person in a simple process.

(5) The control device 202 is configured in such a manner as to substitute a numerical value associated with the degree of functional impairment for the degree, for each cognitive function of the brain of the target person, multiply the substituted numerical value by a weight value assigned to each cognitive function of the brain, and accordingly convert the degree of functional impairment into a numerical form for each cognitive function of the brain of the target person. Consequently, if a high weight value is set for a function that is highly likely to influence the assessment of the driving aptitude among the cognitive functions of the brain, it is possible to assess the driving aptitude of the target person with high accuracy, considering a possibility that the degree of impairment of each cognitive function influences the assessment of the driving aptitude.

—Modifications—

The driving aptitude assessment system of the above-mentioned embodiment can also be modified as follows:

(1) In the above-mentioned embodiment, the example has been described in which the diagnostic terminal 100 and the driving aptitude assessment apparatus 200 are connected via the communications line, and the control device 202 of the driving aptitude assessment apparatus 200 receives an instruction of the diagnostic terminal 100, and assesses the driving aptitude of a target person. However, the driving aptitude assessment apparatus 200 may be used singly. It may be, for example, configured in such a manner that a diagnoser who diagnoses the driving aptitude of a target person operates the driving aptitude assessment apparatus 200, and provides an instruction to start assessing the driving aptitude of the target person, and the control device 202 outputs an assessment result to a display device connected to the driving aptitude assessment apparatus 200 and displays the assessment result. Consequently, it is possible to construct a client-server or cloud assessment system by connecting the diagnostic terminal 100 and the driving aptitude assessment apparatus 200 via the communications line while it is also possible to use the driving aptitude assessment apparatus 200 as a standalone apparatus by using the driving aptitude assessment apparatus 200 singly.

(2) In the above-mentioned embodiment, the example has been described in which the control device 202 assesses the degree of functional impairment of the brain of a target person on the basis of a result of a neuropsychological test of and head image data of the target person, and assesses the driving aptitude of the target person. However, the control device 202 may be configured in such a manner as to, if there is only information of one of a result of a neuropsychological test and head image data of a target person, assess the degree of functional impairment of the brain of the target person on the basis of the existing information, and assess the driving aptitude of the target person.

Unless the characteristic functions of the present invention are impaired, the present invention is not at all limited to the configuration in the above-mentioned embodiment. Moreover, the configuration may be a combination of the above-mentioned embodiment and plurality of modifications.

The contents of the disclosure of the following basic priority application are incorporated herein by reference.
Japanese Patent Application No. 2018-16993 (filed on Feb. 2, 2018)

DESCRIPTION OF REFERENCE SIGNS

10 Driving aptitude assessment system
100 Diagnostic terminal
101 Operating member
102 Connection interface
103 Control device
104 Storage medium
105 Display device
200 Driving aptitude assessment apparatus
201 Connection interface
202 Control device
203 Storage medium

The invention claimed is:

1. A driving aptitude assessment apparatus comprising:
functional impairment degree assessment means configured to assess the degree of functional impairment of a brain of a target person on the basis of test result information indicating a result of a neuropsychological test administered to the target person and head image data obtained by tomography of a head of the target person; and
driving aptitude assessment means configured to assess the driving aptitude of the target person on the basis of an assessment result by the functional impairment degree assessment means,
wherein upon an assessment result based on the test result information and an assessment result based on the head image data being different, the functional impairment degree assessment means assesses the assessment result of which degree of functional impairment is severer to be the degree of functional impairment of the brain of the target person.

2. The driving aptitude assessment apparatus according to claim 1, wherein the functional impairment degree assessment means assesses the degree of functional impairment of the brain of the target person for each cognitive function of the brain, on the basis of the test result information and the head image data.

3. The driving aptitude assessment apparatus according to claim 2, wherein the cognitive functions of the brain include a memory and spatial learning function, a memory storage and retrieval function, a memory and sensory perception function, an executive function, and an information processing function.

4. The driving aptitude assessment apparatus according to claim 2, wherein the driving aptitude assessment means converts the degree of functional impairment into a numerical form for each cognitive function of the brain of the target person, compares a total value of the numerical form with a preset threshold, and assesses the driving aptitude of the target person.

5. The driving aptitude assessment apparatus according to claim 4, wherein the driving aptitude assessment means substitutes a numerical value associated with the degree of functional impairment for the degree, for each cognitive function of the brain of the target person, multiplies the substituted numerical value by a weight value assigned to each cognitive function of the brain, and converts the degree of functional impairment into a numerical form for each cognitive function of the brain of the target person.

6. A driving aptitude assessment system comprising:
functional impairment degree assessment means configured to assess the degree of functional impairment of a brain of a target person on the basis of test result information indicating a result of a neuropsychological test administered to the target person and head image data obtained by tomography of a head of the target person; and
driving aptitude assessment means configured to assess the driving aptitude of the target person on the basis of an assessment result by the functional impairment degree assessment means,
wherein upon an assessment result based on the test result information and an assessment result based on the head image data being different, the functional impairment degree assessment means assesses the assessment result of which degree of functional impairment is severer to be the degree of functional impairment of the brain of the target person.

7. The driving aptitude assessment system according to claim 6, wherein the functional impairment degree assessment means assesses the degree of functional impairment of the brain of the target person for each cognitive function of the brain, on the basis of the test result information and the head image data.

8. The driving aptitude assessment system according to claim 7, wherein the cognitive functions of the brain include a memory and spatial learning function, a memory storage and retrieval function, a memory and sensory perception function, an executive function, and an information processing function.

9. The driving aptitude assessment system according to claim 7, wherein the driving aptitude assessment means converts the degree of functional impairment into a numerical form for each cognitive function of the brain of the target person, compares a total value of the numerical form with a preset threshold, and assesses the driving aptitude of the target person.

10. The driving aptitude assessment system according to claim 9, wherein the driving aptitude assessment means substitutes a numerical value associated with the degree of functional impairment for the degree, for each cognitive function of the brain of the target person, multiplies the substituted numerical value by a weight value assigned to each cognitive function of the brain, and converts the degree of functional impairment into a numerical form for each cognitive function of the brain of the target person.

* * * * *